(12) United States Patent
Chowdhury

(10) Patent No.: US 9,999,597 B2
(45) Date of Patent: Jun. 19, 2018

(54) FORMATION OF PARTICLE STRUCTURES

(71) Applicant: NDM Technologies Limited, Loughborough (GB)

(72) Inventor: Dewan Fazlul Hoque Chowdhury, Loughborough (GB)

(73) Assignee: NDM Technologies Limited, Loughborough (GB)

(*) Notice: Subject to any disclaimer, the term of this patent is extended or adjusted under 35 U.S.C. 154(b) by 263 days.

(21) Appl. No.: 14/763,452

(22) PCT Filed: Jan. 24, 2014

(86) PCT No.: PCT/GB2014/050191
§ 371 (c)(1),
(2) Date: Jul. 24, 2015

(87) PCT Pub. No.: WO2014/114946
PCT Pub. Date: Jul. 31, 2014

(65) Prior Publication Data
US 2015/0359741 A1 Dec. 17, 2015

(30) Foreign Application Priority Data
Jan. 26, 2013 (GB) .................................. 1301385.9

(51) Int. Cl.
*A61K 9/14* (2006.01)
*A61K 9/00* (2006.01)
(Continued)

(52) U.S. Cl.
CPC ..... *A61K 9/14* (2013.01); *A61J 3/00* (2013.01); *A61J 3/02* (2013.01); *A61K 9/0014* (2013.01);
(Continued)

(58) Field of Classification Search
None
See application file for complete search history.

(56) References Cited

U.S. PATENT DOCUMENTS 2,565,491 A    8/1951  Francis, Jr.
4,777,073 A *  10/1988 Sheth .................. B29D 7/01
                                            264/288.4
(Continued)

FOREIGN PATENT DOCUMENTS

JP   2011-517589      6/2011
WO   WO 2009/120361   10/2009
WO   WO 2012/020261   2/2012

OTHER PUBLICATIONS

Castro, Jospeh, "Silicon or Silicone: What's the Difference?", Live Science, Jun. 20, 2013, accessed at livescience.com on Jul. 26, 2017.*

(Continued)

*Primary Examiner* — Alison L Hindenlang
*Assistant Examiner* — Jamel M Nelson
(74) *Attorney, Agent, or Firm* — McCracken & Gillen LLC

(57) ABSTRACT

Irregular, angular particles are produced by a manufacturing method that comprises forming a film on a substrate and then stretching the substrate along one or more axes to fracture the film into particle structures. The substrate may be moved continuously along a production line as the film is formed and may be stretched by accelerating that movement. The substrate may comprise a surface with elevated patterns to control the fracturing of the film. The particles are particularly suitable for the transdermal delivery of a biologically active substance into the body of a patient.

8 Claims, 4 Drawing Sheets

(51) Int. Cl.
*A61J 3/00* (2006.01)
*A61J 3/02* (2006.01)
*A61M 37/00* (2006.01)

(52) U.S. Cl.
CPC ... *A61K 9/0021* (2013.01); *A61M 2037/0053* (2013.01)

(56) References Cited

U.S. PATENT DOCUMENTS

| | | |
|---|---|---|
| 2010/0196435 A1 | 8/2010 | Freeman et al. |
| 2011/0097548 A1* | 4/2011 | Bhandari ............ B32B 15/082 428/164 |
| 2012/0086331 A1* | 4/2012 | Kobayashi ............ H01L 51/504 313/504 |
| 2012/0247389 A1* | 10/2012 | Yoshida ................ C23C 16/46 118/719 |
| 2013/0068410 A1* | 3/2013 | Donohue ............ C23C 14/0005 164/72 |

OTHER PUBLICATIONS

European Patent Office International Search Report dated Jun. 4, 2014, for PCT/GB2014/050191 filed Jan. 24, 2014, Applicant, NDM Technologies Limited (2 pages).

Japanese Office Action and English-language translation, dated Jul. 5, 2016, for Japanese Application No. 2015-554250, Applicant, Kasai et al. (7 pages).

* cited by examiner

FORMATION OF PARTICLE STRUCTURES

TECHNICAL FIELD

The invention relates to the preparation of particle structures with applications in the field of delivery of drugs into the body of a patient. In particular, it relates to methods of preparation of irregular, angular microstructures which may be used for drug delivery applications including direct insertion into the skin of a patient. However, the invention may also be applied to the preparation of particle structures using suitable formulations for a wide range of other fields, such as preparation of additive materials for composites, and in food applications.

For the sake of brevity, the term "drugs" is used in this specification to refer to any chemically or biologically active substance that may need to be introduced into the body of a patient to provide a therapeutic or cosmetic effect. The patient may be human or a non-human animal.

BACKGROUND OF THE INVENTION

Numerous methods have been used to produce microneedles attached to a substrate for the purpose of application through the skin of a patient. These are uniform regular structures produced using various moulding techniques. It has been proposed that the microneedles themselves may be produced from a formulation of the drug. On application to the skin of a patient, the needles break and remain in the skin, where the formulation dissolves and the active substance is absorbed into the blood stream.

In published literature it is known that particles such as platelets and other shapes have also been produced using various techniques including lithographic and micro-moulding, micro-replication and imprinting techniques, in order to produce particles of defined (and often large) surface areas for enhanced drug solubility for example, with subsequent incorporation into depot injections, oral solutions or compressed into tablets and filled into capsules.

The main barrier to the delivery of drugs through the skin is the stratum corneum, which is a tough outer layer of dead skin cells. A further route for delivery of a drug into the body of a patient, especially for treatment of diseases of the eye, is through the surface of the cornea of the eye. For the purposes of this specification, that route is included within the term "transdermal".

In conventional tabletting, the granules are produced using an elaborate process of producing a wet or dry mass of the drug and excipients followed by size reduction using mechanical means amongst others, and using spray-drying, freeze-drying or further processing as required such as coating the particles, followed by their subsequent storage either in the granular form (for enhanced dissolution) or compressed into tablets (since the granules provide the correct bulk density and compression properties for processing into tablets).

Particles of drug are also described in published patent application WO 2012/020261, which further describes a method for producing said angular particles by forming a film of the drug which is dried and size reduced using some form of grinding technique. Particles of the drug formulation may be produced as individual separate entities as described in WO 2012/020261. These particles may be used for direct insertion into the skin or cornea of a patient, or the particles may be used as a means of enhancing the surface area and thus solubility of a drug. The method of preparing such particles through the formation of a film followed by drying and milling will lead to a large range of particle sizes/lengths. It may be preferable to produce such particles within narrow dimensional profiles using a process that leads to high yields within narrower particle size profiles.

SUMMARY OF THE INVENTION

The invention provides an apparatus and method for the preparation of particle structures of a drug formulation.

Specifically, the invention provides a method of manufacturing particle structures, the method comprising the steps of forming a film on a substrate; and stretching the substrate to fracture the film into particle structures.

The invention further provides an apparatus for manufacturing particle structures, the apparatus comprising: a substrate; means for depositing a film on the substrate; means for moving the substrate past the depositing means and from a first location to a second location; and means for stretching the substrate as it moves from the first location to the second location to fracture the film into particle structures.

The structures formed in accordance with the invention may be soluble or biodegradable in the body, and the particle structures may be rigid, and may be regular or irregular in shape and may be angular so that they are capable of penetrating the surface of the skin or of a cornea of the patient.

By "irregular", it is meant that the structures are not formed to have a consistent geometry on all planes/surface features/topography as would be the case for micro-moulding, micro-replication, or micro/nano-imprinting for example. The particles do not need to be precision engineered with a defined aspect ratio and instead can be produced within a narrow dimensional range and the consistency of the size range will lead to high yields thus making the process economically viable from a mass production perspective.

By "angular" it is meant that the structures have sharp edges and/or corners that can lodge in pores and crevices in the surface of the skin. When subjected to pressure, the angular particles can be forced into the stratum corneum of the skin (or the surface of the cornea) to be available for deeper absorption into the body. The stratum corneum is several tens of microns thick so it follows that particles containing drug need only breach this barrier of, e.g. 40 microns. According to a preferred definition of "angular", at least 50% of the particles have at least one sharp corner, where a sharp corner is one characterized in that for every pair of faces of the particle that meet at the corner, the angle at which they meet is no greater than 90°. Thus the corner is at least as sharp as the corner of a cube. Another aspect of sharpness of the corners is their radius of curvature. That is preferably much less than the overall size of the particle: typically no more than a few microns and in any case less than a few tens of microns. The smaller radius or curvature is preferred where the particles are intended for direct insertion into the skin, whereas larger radii of curvature are adequate where the structure is intended for incorporation into another vehicle such as capsule, tablet or liquid whereby the dimensional features of the particle may aid the dissolution of the drug from the structure and thus the bioavailability of the drug.

The preparation preferably comprises a biologically active substance that has a therapeutic or cosmetic effect. The preparation may comprise a formulation consisting purely of the drug/active itself, or containing at least one excipient with the active substance, the excipient being chosen to give the particles the required physical and chemical properties. Examples of such excipients include carbohydrates, biodegradable polymers, and standard excipients known in the state of the art used in pharmaceutical dosage forms.

Alternatively, the preparation may be a substance that is biologically inert (but still biocompatible and biodegradable). Its purpose would be to disrupt the stratum corneum of the patient in order to enhance the subsequent transdermal delivery of an active substance into the body of the patient, or to act as an intermediate in the preparation of a dosage formulation such as a tablet, or drug carrier particles for potent drugs filled in capsules for example.

In accordance with the invention, particles that are sufficiently angular to be pressed through the stratum corneum of a patient's skin, or irregular microstructures within defined size ranges, may be produced by controlled fragmentation from a formed film. The formulations of, typically, an active ingredient combined with one or more excipients and a binder may first be produced as a thin film of aggregate cast onto a substrate then passed through a drying tunnel in a similar manner to a known method of manufacturing membranes. The film can be made as little as less than 10 microns in thickness. The substrate upon which the formed film is produced is then gently stretched to fracture the film along natural planes of weakness and produce microstructures (particles) ranging in maximum diameter from nanometers to hundreds of micrometers. Depending on the mechanical properties of the film, the process may form not only fractures extending between opposite faces of the film but also fractures within the thickness of the film, thereby creating particles with a maximum diameter smaller than the film thickness.

The mean size of the particles may be between 100 nm and 1 mm. It is preferably between 1 μm and 100 μm. At the lower end of these ranges, the particles are microstructures much smaller than the types of microneedles that can be manufactured, which aids their absorption by the body. The preferred measure for the size of the particles is their tip radius and maximum diameter. However it will be appreciated that with the appropriate adjustments to the processing parameters, described below, it is possible to produce larger particles with lengths greater than 1 mm and in the range of 1-5 mm for other applications. One such application may be to mimic the performance of granules used for tabletting.

The process of preparing the particles typically entails four key steps: production of a wet mix, drying the mix, size reduction, and size separation according to the desired particle size range. Drying may be conducted using hot air, dry oven, ambient air drying or vacuum drying, according to the thermal sensitivities of the mix/drug. The preparation may use formulations already reported in scientific and patent literature for the production of microneedles containing an active ingredient. The formulation may comprise a single component, i.e. just the drug itself, if the drug has the right mechanical properties upon being wetted using a suitable solvent, dried and fractured to the desired particle size range. In the more common event that the drug alone does not have the right properties when processed in this way, it may be combined with one or more excipients that will impart to it such mechanical properties when processed as described. One of the objectives is to produce tough, sharp microstructures that will permeate the skin and dissolve on contact with the interstitial fluid. However for alternative uses, fractured particles of a defined dimensional range may be adequate for the intended purpose. The fracture will lead to relatively uniform structures with irregular shapes and surfaces, which will lead to enhanced or controlled dissolution of drug from the microstructure, due to the increased surface area and particle density properties.

Excipients that may be used in combination with the drug to impart the desired mechanical and chemical properties would have a number of key functions. One such function is to enhance the binding of the drug particles such that a strong cohesive bond exists that prevents the particles from eroding after their production and on storage, i.e., to reduce the friability of the particles. This class of agents is classified as binding agents. Examples of binding agents include acacia, alginic acid, carboxymethylcellulose, compressible sugar, ethylcellulose gelatin, liquid glucose, methylcellulose, povidone, and pregelatinized starch, amongst others. The amounts of such agents that would be incorporated into a mixture have been well established and documented over several decades of their use primarily in the formulation of tablets and latterly in granule production.

Another key function of any excipient would be to cause hardening of the particles. Examples of hardening agents include hydrogenated vegetable oils, stearic acid, and silicone. Once again the use of these materials and their compositions is well established in literature, in particular for producing hardened shells and coatings on tablets and caplets, for controlled release and drug taste masking.

A third important class of excipients that may be incorporated into such a system are bulking agents. In some instances the bulking agent would serve multiple functions, and may also impart some binding and hardening properties. These are primarily carbohydrates such as maltose, dextrose, fructose, glucose, trehalose, starch, and cellulose. Biodegradable polymers may also be used, in particular those such as the hydrogels.

Additional excipients may include solvents, lubricants to aid powder flow, viscosity modifying agents, dispersing agents, solubilising agents, polymers to modify drug release and absorption properties, and preservatives.

It has been found experimentally that sucrose is a particularly effective excipient for the formation of suitably shaped particles according to the present invention. The sucrose was mixed with an active ingredient such as ibuprofen or diclofenac, together with sufficient water as a binding agent, and prepared according to the thin film method previously described. With ratios of sucrose:drug greater than 60:40, highly angular particles were produced. The particles remained hard during storage, with little tendency to absorb moisture. It is clearly desirable to use no more excipient than is necessary so a maximum ratio of 20:1 is envisaged.

The substrate used for forming the film plays a pivotal role in this invention. The substrate may have the following properties: the surface texture may be rough or smooth. The surface may be patterned so that the planes of fracture will lead to particle structures of a desired geometry type and/or control over the length of the resultant structures, whereas the fracture strain coupled with relative adhesivity between the formed film and substrate, and degree of stretching of the underlying substrate will dictate the width of the fractured structure. The materials of construction will be such that it allows the substrate to be stretched by at least a percentage elongation, preferably uniformly across the cross sectional surface area, such that the underlying film is able to fracture; the greater the percentage elongation the smaller the fractured structures.

The size of the fractured structures is also dictated by the degree of dryness of the formed film, whereby a small percentage moisture/solvent in the film coupled with very high degree of stretch (up to or greater than 100% strain)

leads to the smallest and finest (highest aspect ratio) structures. It follows that there is also a balance between the adhesivity of the formed film to the substrate and the ability of the substrate to stretch away from the formed film. References to a solid film therefore include a solid film that may be completely dry or partially dry prior to fracture of the film. The relationship is that the adhesion force of the formed film to the substrate should be greater than the tensile strain required to fracture the formed film for a given size of structure. More specifically, in the case of a fully dried formed film, the strength of the adhesive bond between the formed film and the substrate upon which it is formed will be such that the film cannot be scraped off the surface of the substrate if the opposite face of the substrate was adhered to a solid un-stretchable material. In the case of a partially dried film the adhesion forces whilst they are not required to be as high as for the fully dried film, the frictional force between the formed film and the substrate must be greater than the strain forces applied to the substrate at low percentage stretch to lead to fracture planes that will produce particle structures of the smaller size range instead of merely allowing the formed film to slip over the substrate.

Examples of materials used for the substrate are sheets of silicone film that are highly elastic with tensile strains of over several hundred percent possible. A highly plastic material with virtually zero/very low elasticity that has also been used for this application is the plastic film Parafilm®. Additionally Hostaphan® RN23 (from Mitsubishi films), a polyester backing membrane, was also used. The latter exhibits very little elasticity, very low plastic yield and has a very high break force, >100 N/mm².

The other key parameter that must be controlled for is the rate and extent of stretching of the substrate. It will be understood that the stretching may be in one or more directions, either in series or simultaneously, and the extent of stretching may be variable along different axes, or lengths of the formed film.

It will also be understood that whilst the main subject of the invention relates to the preparation of particles for applications in the aforementioned field, the method may also be applied to the preparation of particle structures using suitable formulations for a wide range of other fields, such as preparation of additive materials for composites, and food applications.

It will also be understood that whilst the formation of the film above refers to a single film, it may be desirable to produce one or more layers having different formulations that are bonded together either by virtue of the chemical properties of the layers, or using a physical means of bonding such as optical radiation or ultrasonic energy, or using chemical means such as chemical adhesives, prior to the film being fractured. This may be desirable for instance where a drug is intended to be sandwiched between two layers that act as a rate controlling surface to allow controlled dissolution or release of the drug from the finally formed particle, or where two or more components are incompatible or lead to stability issues if they are combined into a single film.

DETAILED DESCRIPTION OF THE INVENTION

Figure 1:
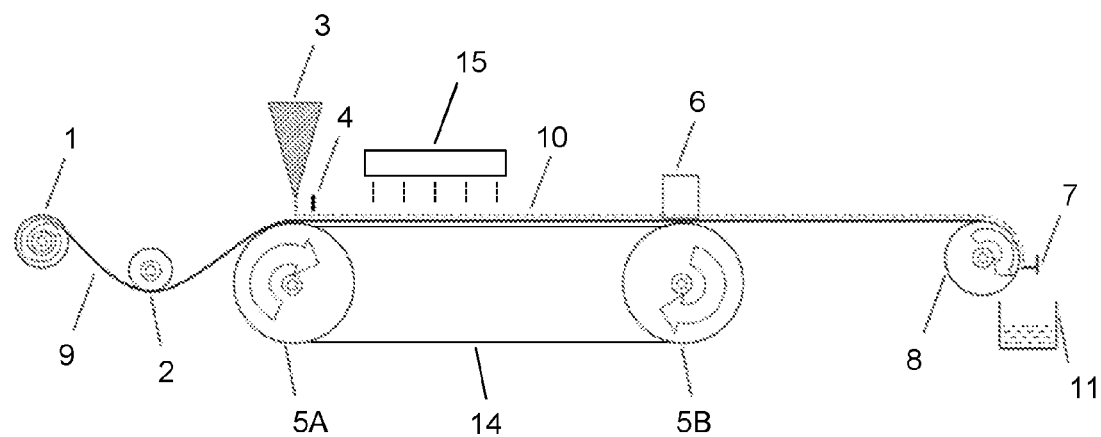
FIG. 1 schematically shows a production line for carrying out a manufacturing method in accordance with the invention.

FIG. 1 schematically shows a coating line whereby the mixture 3 is coated on to a substrate 9 to form a film 10. The film 10 may be a solid aggregate of a formulation (that may be soluble or biodegradable in the body, depending upon the intended method of application). The active agent and the excipient are dissolved in a suitable medium, the medium being defined as a vehicle, to produce the mixture 3 as a liquid, paste or solution. The mixture 3 will be a homogenous or heterogenous mixture of the various components, of which the minimum number of components will be the active agent and a solubilising solution medium or dispersion medium. The medium may be organic or non-organic in nature including but not limited to deionised water, buffer solution (such as phosphate or citrate buffer), or ethanol, ethyl acetate or other organic solvent.

The mixture 3 is cast as a thin film 10, whereby the film is defined as a quantity of the mixture spread over a surface or substrate where the thickness of the cast mixture ranges from a few microns to a few millimeters. The vehicle will partially or completely evaporate to leave the solid mass as a film spread over the substrate to a thickness lower than the thickness of the original cast mixture. The casting process may be a simple knife over roller casting that is used as a standard process in the production of transdermal drug patches for example (such as nicotine patches). The film 10 may alternatively be extruded as a solid mass to create a film spread over the substrate 9. Following drying the mass of the film may be minimally altered, thus the thickness of the final film being comparable to the thickness of the extruded mass. The film 10 may alternatively be cast by spraying the mixture directly onto a suitable substrate 9 in a controlled way to provide the desired thickness profile of the cast film, followed by drying.

The substrate 9 is fed from a roll 1, strained using a tension rod 2, and travels along a conveyor 14 driven by rollers 5A, 5B, where it is dried using one or more means 15, including but not limited to air drying, heat drying, forced air drying, infra-red drying, micro-wave drying, or a combination of these. The substrate is constrained to move at the speed of the conveyor 14 by compression blocks 6 above roller 5B, and is then stretched from roller 5B onwards to roller 8 by rotating the roller 8 at a speed that is greater than the speed of transit of the film 10 along the conveyor 14. This causes the substrate 9 to stretch as it exits the conveyor system and accelerates between rollers 5B and 8, which causes the formed film 10 to fracture into particle structures. Means 7 are provided for the particle structures to be subsequently scraped/brushed/air-jetted 7 off the substrate 9 and collected in a collection chamber 11.

The substrate 9 upon which the film 10 is cast may be a solid or semi-solid material. In this invention it is a further requirement that the film is cast on a substrate that can be stretched along one or more axes. The amount of strain it should undergo may be less than 1%, up to several percent and, in some applications, the substrate may be stretchable to several times its original size. When the film-forming mixture is cast upon this substrate 9 and suitably dried to a solid film 10, and the substrate is then stretched along one or more of its axes, the deposited film will fracture along its natural planes of fracture. The extent of the strain will ensure the film 10 has fractured evenly throughout.

Figure 2:
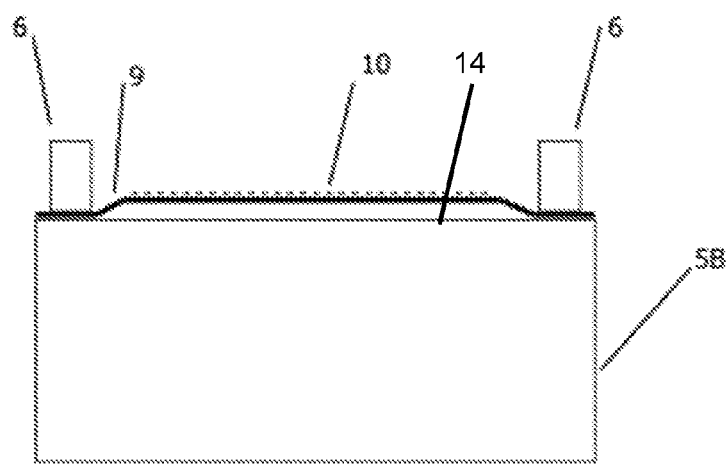
FIG. 2 shows a cross-section through the production line of FIG. 1.

FIG. 2 shows a cross section of the regions where the coating substrate 9 is gripped between the roller 5B and compression blocks 6 such that the substrate 9 between this junction and the final roller 8 can be stretched by modulating the speed of the final roller, allowing the formed film 10 to fracture. It will be readily understood that the film 10 could also be stretched in the direction perpendicular to the travel of the film, or in both directions simultaneously (not shown here), and the compression means may be pneumatic, spring loaded, solid or other, and the degree of stretching may be constant or may be variable. The stretching need not be confined to a plane. As the substrate 9 passes over the final roller 8, the film 10 formed on its upper surface will undergo a degree of stretching determined by the curvature of the roller 8 and the thickness of the substrate 9. The roller 8 could also be curved in the transverse direction to form a part-spherical or barrel-shaped surface (not shown), which would cause additional stretching of the substrate and the film in the direction transverse to the direction of movement.

Figure 3:
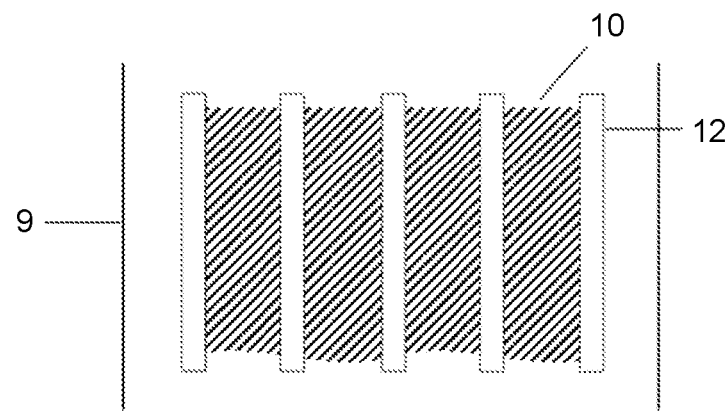
FIG. 3 shows a plan view of a substrate suitable for use in a method according to the invention.

FIG. 3 shows a plan view of the substrate 9 coated with the film 10 whereby the substrate contains elevated patterns 12 (in this case raised strips) or means of separating regions within the substrate to allow the film to be formed in the desired pattern to allow the desired particle structures to be formed upon stretching the underlying substrate.

Figure 4:
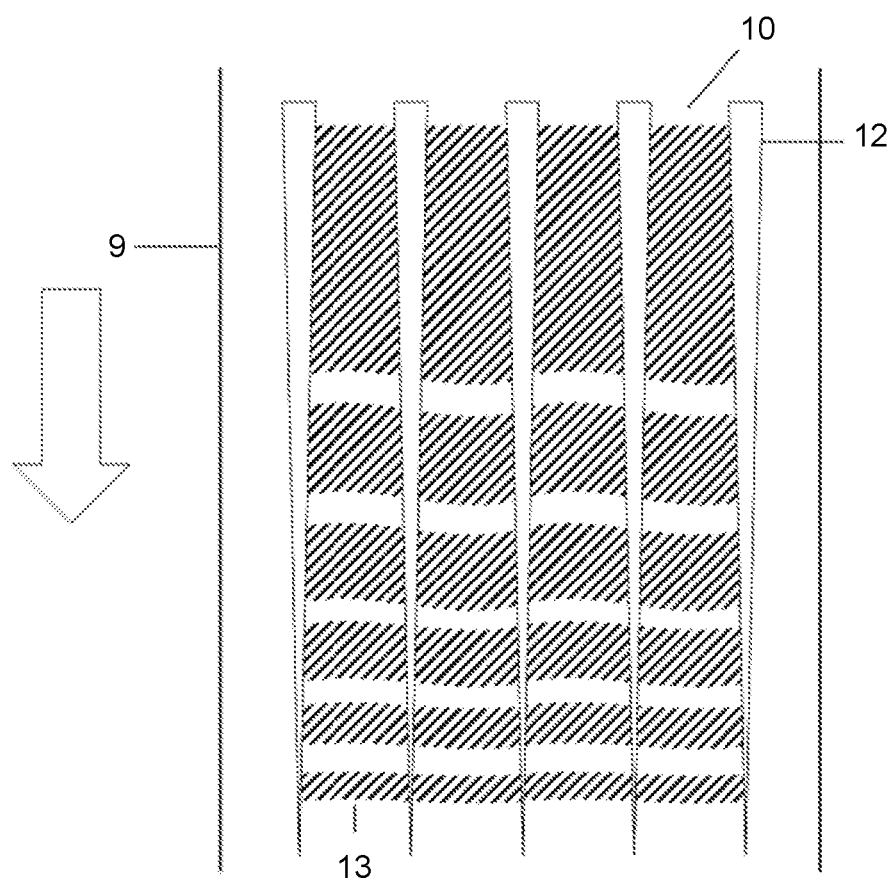
FIG. 4 shows a plan view of the substrate of FIG. 3 to illustrate how it stretches when used in a method according to the invention.

FIG. 4 is a depiction of the substrate 9 of FIG. 3, with the block arrow showing the direction of travel of the conveyor, thus direction of travel of the film 10 and underlying substrate 9. The Figure indicates the raised patterns 12 also elongating or stretching as the film is stretched, leading to the gradual fracture of the film and the formation of particle structures 13. In this case the length of the particle structures is controlled and defined by the distance between the elevated strips 12 on the substrate. The raised strips 12 may be formed of the same material as the substrate (and may possibly be a continuous part of the substrate) or may be formed of a different plastic or rubber or other type of material that allows it to stretch with the underlying substrate either to the same extent or with some differential. A difference between the extent of stretch between the substrate and the strip may assist the particle structures to readily dislodge from the substrate after their formation. These patterns 12 on the substrate 9 may be designed to be the same height as the intended coating height of the film, and may be from 10's of microns to millimeters in terms of feature size. It will be understood that whilst longitudinal strips have been shown here, these are for illustration purposes and different patterns may be used with different directions of stretch to form particle structures of different geometries.

Figure 5:
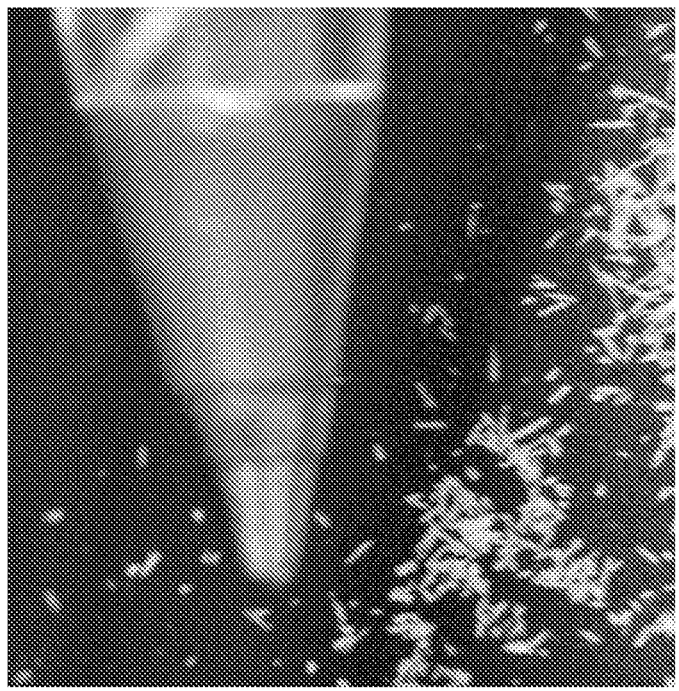
FIG. 5 is an image of a first example of a formulation prepared using a method according to the invention.

FIG. 5 shows an image of a formulation prepared using the above technique containing sucrose and diclofenac sodium, prepared using a substrate that is highly stretchable (silicone polymer membrane). The tip of a ball point pen is included for scale.

Figure 6:
FIG. 6 is an image of a second example of a formulation prepared using a method according to the invention.

FIG. 6 shows an image of the same formulation as used in FIG. 3, prepared using a substrate having a tensile strength of greater than 100 N/mm$^2$ (Hostaphan RN23 backing membrane).

Figure 7:
FIG. 7 is a further image showing the particle structures of FIGS. 5 and 6 side by side.

FIG. 7 shows the particle structures as prepared in FIGS. 5 and 6 respectively, side by side. This demonstrates that the lower the percentage strain of the substrate 9, for a given drug film formulation, the larger the resulting fragmented structures. Substrates that readily stretch, exhibiting either plastic or elastic behaviour, have been shown to allow the formation of structures with diameters less than 10 μm. Substrates 9 that readily stretch allow the formed film 10 to be fractured over very small distances since the greater the degree of extension of the underlying substrate, the more regions there are where the formed film is able to fracture. Furthermore if the formed film is not completely dried and has some residual moisture/solvent then it has been found that the film can fracture with a higher degree of uniformity, to produce more uniform fragments of the particle structures, which can then be subsequently dried further to provide the correct/desired mechanical strength.

The invention claimed is:

1. An apparatus for manufacturing particle structures, the apparatus comprising:
    a substrate;
    means for depositing a film on the substrate;
    a conveyor for moving the substrate past the depositing means and from a first location to a second location; and
    means for stretching the substrate as it moves from the first location to the second location to fracture the film into particle structures.

2. The apparatus according to claim 1, wherein the means for stretching comprises a first roller, which drives the substrate to move at a first speed at the first location, and a second roller, which drives the substrate to move at a faster, second speed at the second location.

3. The apparatus according to claim 2, wherein the means for stretching further comprises means for compressing the substrate against the first roller.

4. The apparatus according to claim 1, further comprising means for drying the film as it moves from the depositing means to the first location.

5. The apparatus according to claim 1, wherein the substrate comprises a surface with elevated patterns.

6. The apparatus according to claim 5, wherein the elevated patterns comprise raised longitudinal strips.

7. The apparatus according to claim 1, wherein the substrate is formed from a silicone polymer.

8. The apparatus according to claim 1, wherein the substrate has a tensile strength greater than 100 N/mm$^2$.

* * * * *